US012661469B2

(12) United States Patent
Veasey et al.

(10) Patent No.: US 12,661,469 B2
(45) Date of Patent: Jun. 23, 2026

(54) TRACHEOSTOMY TUBES AND THEIR MANUFACTURE

(71) Applicant: SMITHS MEDICAL INTERNATIONAL LIMITED, Ashford (GB)

(72) Inventors: Neil Steven Veasey, Ashford (GB); Christopher John Woosnam, London (GB); Andrew Thomas Jeffrey, Marsh (GB); Timothy Bateman, Hythe (GB)

(73) Assignee: ICU Medical International Limited, Ashford (GB)

( * ) Notice: Subject to any disclaimer, the term of this patent is extended or adjusted under 35 U.S.C. 154(b) by 734 days.

(21) Appl. No.: 17/916,889

(22) PCT Filed: Apr. 6, 2021

(86) PCT No.: PCT/GB2021/000038
§ 371 (c)(1),
(2) Date: Oct. 4, 2022

(87) PCT Pub. No.: WO2021/214423
PCT Pub. Date: Oct. 28, 2021

(65) Prior Publication Data
US 2023/0181853 A1 Jun. 15, 2023

(30) Foreign Application Priority Data

Apr. 24, 2020 (GB) ..................................... 2006052

(51) Int. Cl.
*A61M 16/04* (2006.01)
*F16B 17/00* (2006.01)
(52) U.S. Cl.
CPC .... *A61M 16/0465* (2013.01); *A61M 16/0497* (2013.01); *F16B 17/006* (2013.01); *A61M 2207/10* (2013.01)

(58) Field of Classification Search
CPC ............ A61M 16/0465; A61M 16/047; A61M 16/0497; A61M 16/0683; A61M 16/0694;
(Continued)

(56) References Cited

U.S. PATENT DOCUMENTS 586,770 A * 7/1897 Kempshall ................ B64B 1/00
156/196
780,526 A * 1/1905 Reitz ........................ B26B 13/28
30/266
(Continued)

FOREIGN PATENT DOCUMENTS

CA 2124165 A1 * 11/1995
DE 202013004245 U1 8/2013
(Continued)

OTHER PUBLICATIONS

PCT International Search Report for PCT/GB2021/000038 dated Jul. 29, 2021.
PCT Written Opinion for PCT/GB2021/000038 dated Jul. 29, 2021.

*Primary Examiner* — Kathryn E Ditmer
(74) *Attorney, Agent, or Firm* — Louis Woo

(57) ABSTRACT

The neck flange 3 of a tracheostomy tube is of a soft plastics such as silicone and has neck tie or suture openings 35 at opposite ends reinforced to prevent damage to the flange. The openings are reinforced by tubular inserts 38 of a harder plastics. The patient end of each insert has an enlarged, radially extending head 41 sitting flush in an enlarged recess 43 around the patient end of each opening. The opposite end of each insert also has an enlarged head 42 overlapping the flange but formed after the insert has been inserted in the flange. The opposite end head 42 may be heat formed from the end of the insert or may be a separate component clipped onto the end of the insert.

5 Claims, 4 Drawing Sheets

(58) Field of Classification Search
CPC ........................ A43C 5/00; A42B 3/08; A44B
13/0058–0094
See application file for complete search history.

(56) References Cited

U.S. PATENT DOCUMENTS

| | | | | |
|---|---|---|---|---|
| 848,215 A * | 3/1907 | Babb ...................... | A61G 1/013 |
| | | | 5/117 |
| 2,300,912 A * | 11/1942 | Dodge .................. | A62B 18/00 |
| | | | D24/110.2 |
| 2,957,196 A * | 10/1960 | Delgadillo ............... | F16B 5/01 |
| | | | 29/523 |
| 3,099,057 A * | 7/1963 | Cook ...................... | F16B 19/10 |
| | | | 411/501 |
| 3,252,493 A * | 5/1966 | Smith ...................... | F16B 5/01 |
| | | | 428/116 |
| 3,395,711 A * | 8/1968 | Plzak, Jr. .......... | A61M 16/0465 |
| | | | 128/200.26 |
| 3,960,437 A * | 6/1976 | Von Heck ................. | B62J 6/20 |
| | | | 359/523 |
| 4,865,792 A * | 9/1989 | Moyer ................... | F16B 43/00 |
| | | | 264/257 |
| 5,026,352 A | 6/1991 | Anderson | |
| 5,054,482 A * | 10/1991 | Bales ................ | A61M 16/0497 |
| | | | 128/207.14 |
| 5,443,064 A | 8/1995 | Theis et al. | |

| | | | | |
|---|---|---|---|---|
| 5,647,107 A * | 7/1997 | Brewster ................... | G09F 7/02 |
| | | | 24/713.6 |
| 5,769,144 A * | 6/1998 | Carter ............... | A44B 13/0076 |
| | | | 411/338 |
| 8,777,537 B2 * | 7/2014 | Fritsch ...................... | F16B 5/02 |
| | | | 411/338 |
| 9,061,379 B1 * | 6/2015 | Mead ....................... | B21J 15/04 |
| 2007/0163600 A1 * | 7/2007 | Hoffman ........... | A61M 16/0683 |
| | | | 128/207.18 |
| 2007/0266470 A1 * | 11/2007 | Lamanna ............... | A62B 18/02 |
| | | | 2/6.3 |
| 2009/0208691 A1 * | 8/2009 | Whitworth ............... | B64F 5/40 |
| | | | 156/391 |
| 2012/0222682 A1 * | 9/2012 | Nguyen ........... | A61M 16/0497 |
| | | | 128/207.17 |
| 2013/0255693 A1 * | 10/2013 | Depel .............. | A61M 16/0465 |
| | | | 29/428 |

FOREIGN PATENT DOCUMENTS

| | | | | |
|---|---|---|---|---|
| DE | 202017000155 U1 * | 3/2017 | ....... A61M 16/4034 |
| EP | 2687149 A1 | 1/2014 | |
| EP | 2777423 A1 * | 9/2014 | .......... A44B 11/006 |
| FR | 2769802 A1 | 4/1999 | |
| GB | 2169372 B * | 9/1988 | |
| IT | B020100115 A1 | 8/2011 | |
| KR | 101614080 B1 * | 4/2016 | ........ A44B 13/0064 |
| WO | WO-2016129285 A1 * | 8/2016 | ........... A61M 16/04 |

* cited by examiner

TRACHEOSTOMY TUBES AND THEIR MANUFACTURE

This invention relates to tracheostomy tubes of the kind including a shaft with a patient end adapted to locate in the trachea and a flange at the machine end of the shaft for securing the tube with a patient's neck, the flange extending outwardly of the shaft and having an opening towards each end.

Tracheostomy tubes are used to enable ventilation or respiration of a patient. They are inserted into the trachea via a surgically formed opening in the neck so that one end of the tube locates in the trachea and the other end locates outside the patient adjacent the neck surface. Tracheostomy tubes are generally used for more long-term ventilation or where it is not possible to insert an airway through the mouth or nose. Various types of different tracheostomy tubes are presently available to suit different needs. The tube may be moulded of a soft material, such as a silicone plastics material, where there is a greater risk of trauma to the tracheal lining, such as in paediatric patients or patients with a damaged trachea. Typically, tubes are made by a one-shot moulding process where the shaft of the tube and the flange by which it is secured to the patient are moulded together an integral, one-piece component. The machine end coupling by which gas connection is made to the shaft is separately moulded from a different, harder material and subsequently attached to the machine end of the shaft and flange sub-assembly. It is desirable for the flange to be moulded from a soft, conformable plastics so that it flexes readily to conform to the surface of the patient's neck. However, flanges moulded of a soft plastics material can create problems in that the material may not be strong enough to ensure that the neck strap or sutures do not tear the flange where it is threaded through the openings used to secure the tube to the patient's neck. In an attempt to reduce this risk, it has been proposed to add an additional reinforcement around the neck strap openings as described in U.S. Pat. No. 9,457,164. Another problem with adding an additional reinforcement member around the neck strap openings is that of ensuring that the reinforcement member does not separate from the flange since any such loose member could be inhaled or provide concern that it has been inhaled.

It is an object of the present invention to provide an alternative tracheostomy tube and a method of manufacturing such a tube.

According to one aspect of the present invention there is provided a tracheostomy tube of the above-specified kind, characterised in that the opening has a radially-enlarged recess around it on at least that side of the flange facing the patient, that the tube also includes a hollow insert of a plastics material harder than that of the flange received in both openings of the flange, each insert having an enlarged head at its patient end received in the recess in the flange and having a thickness equal to the depth of the recess so as to form a smooth patient-facing surface of the flange, that the machine end of each insert is retained with the flange by a radially-extending head overlapping the flange around the opening, and that the hollow insert has a passage along its length through which a neck tie or suture can be extended to secure the tube with the patient's neck.

The flange may have an enlarged recess around each opening on the machine side of the flange. The head at the machine end of each insert is preferably domed. The radially-extending head at one end of each insert may be preformed before insertion in the flange, the radially-extending head at the opposite end being formed after insertion by heat forming from the material of the insert as a single piece with the insert. The preformed head is preferably at the patient end of the insert. Alternatively, the radially-extending head at the machine end of the insert may be provided by a separate member secured with the machine end of the insert. The separate member may be secured with the insert by cooperating clip formations. The inserts are preferably of circular section. The flange may be of silicone.

According to another aspect of the present invention there is provided a method of reinforcing neck tie or suture openings in the flange of a tracheostomy tube wherein the openings have an enlarged recess on the patient side of the flange, characterised in the method includes the steps of providing a hollow insert having a tubular body open at both ends and with a radially-enlarged head at its patient end, inserting the insert into the opening from the patient side of the flange so that the head on the insert locates in the recess and its patient end surface lies flush with the patient end surface of the flange, and subsequently forming a radially-enlarged head at the opposite end of the insert to overlie the machine end surface of the flange around the opening and thereby retain the insert securely with the flange, the tubular body providing a passage through which a neck tie or suture can be extended for use in securing the tube with the patient's neck.

The radially-enlarged head at the opposite end of the insert may be heat formed after insertion in the opening. Alternatively, the radially-enlarged head at the opposite end of the insert may be formed by attaching a separate member to the opposite end of the insert to overlie the flange around the opening.

According to a further aspect of the present invention there is provided a tracheostomy tube having a flange with neck tie or suture openings reinforced by a method according to the above other aspect of the present invention.

A tracheostomy tube and its method of manufacture according to the present invention will now be described by way of example, with reference to the accompanying drawings, in which.

Figure 1:
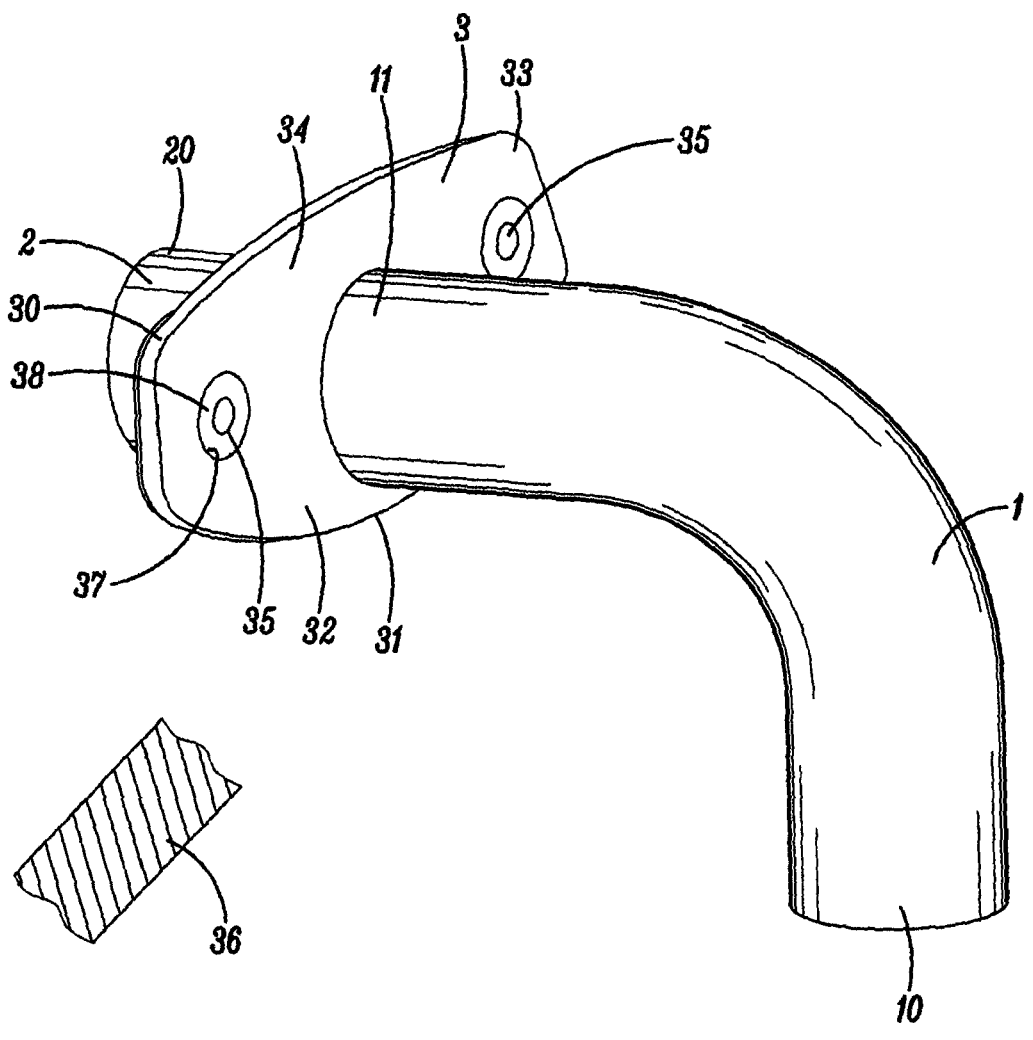
FIG. 1 is a perspective view of the tube from its forward, patient end.

With reference first to FIG. 1, the tube comprises a curved shaft 1 having a patient end 10 adapted for location in the trachea and a rear or machine end 11 adapted to project externally of the neck through the tracheostomy opening. A connector or coupling 2 is attached with the rear end 11 of the shaft 1 and has a male tapered outer surface 20 adapted to make a mating coupling with a female tapered coupling (not shown) at the patient end of a breathing circuit. Alternatively, the coupling may be left open where the patient is breathing unaided. The tube is completed by a flange 3 by which the tube is secured with the patient's neck. The tube is shown without a sealing cuff, but such a conventional cuff and inflation line could be used. The shape and cross-section of the shaft 1 could be of any conventional form. The tube could also include other conventional features such as provision for suctioning.

Figure 2:
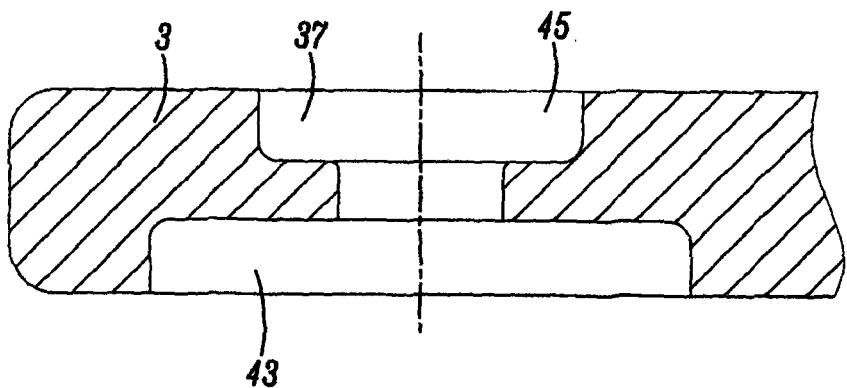
FIG. 2 is a cross-sectional view through a part of the flange before assembly of reinforcing inserts.
Figure 3:
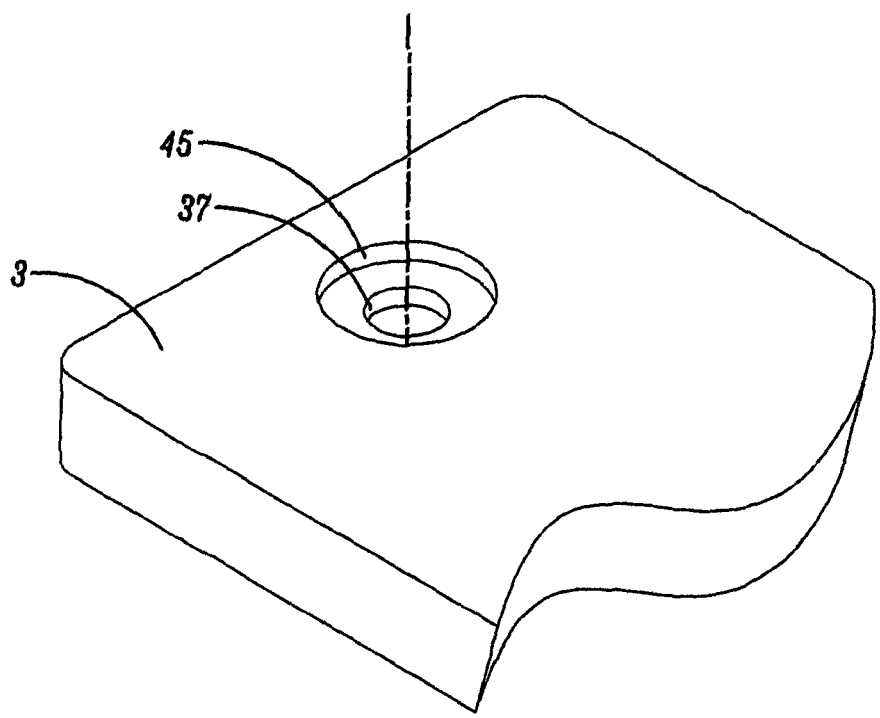
FIG. 3 is a perspective view of the part shown in FIG. 2.
Figure 4:
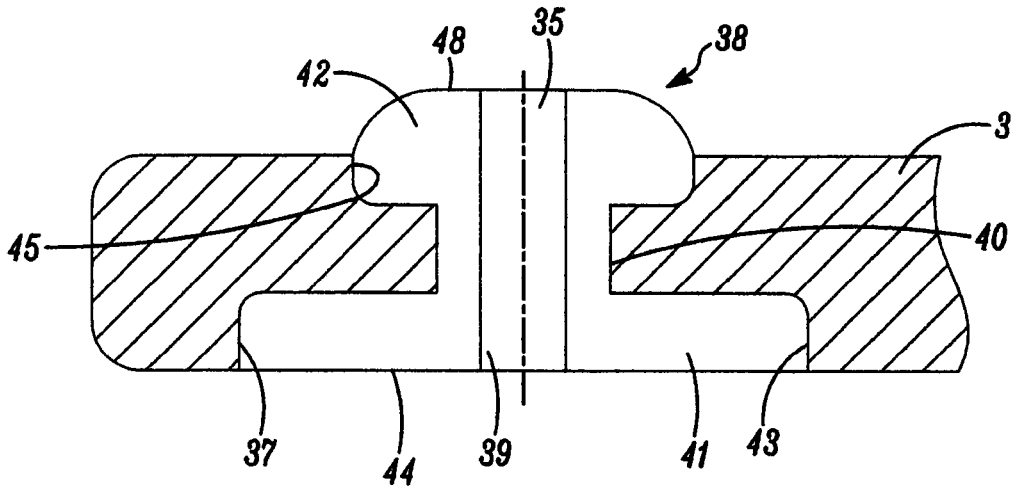
FIG. 4 is a cross-sectional view of a part of the flange showing a reinforcing insert.

The flange 3 has a generally rectangular shape with curved upper and lower sides 30 and 31, and two arms 32 and 33 projecting outwardly from a central region 34. The flange 3 extends in a plane at right angles to both the axis of the coupling 2 and the plane of curvature of the shaft 1. The flange 3 is of a relatively soft, conformable plastics material such as silicone so that it can flex readily to conform to the anatomy of the neck around the tracheostomy and so that it does not chaff the skin of the neck. The flange 3 may be moulded integrally with the shaft 1 as a single piece of the same material or it may be a separate component attached with the shaft and coupling. Towards opposite ends of the flange 3 neck tie or suture openings 35 extend through the thickness of the flange so that a neck tie 36 can be threaded or otherwise secured in the openings. With reference now also to FIGS. 2 to 4 each opening 35 is formed by the combination of an aperture 37 through the flange 3 and a hollow reinforcing insert 38 extending through the aperture and secured with it. The reinforcing insert 38 is of a plastics material harder than that of the flange 3, such as, for example, PEEK, polysulphone, PEBAX or other material capable of being heat formed. It is also preferable, where the flange 3 is made of silicone, that the material of the insert be capable of withstanding the high temperature vulcanisation process of the silicone, and that it be capable of withstanding multiple autoclave cycles (such as up to ten cycles of 121° C. at elevated pressure for 40 minutes per cycle) where the tube is designed for re-use. The inserts 38 have a circular section with a passage or bore 39 extending axially along its length of sufficient size to provide the openings 35 that receive the ends of the neck tie 36. The insert 38 has a central body portion 40 with a pre-formed, radially-extending enlarged disc-shape head 41 at its lower, patient end and an upper head 42 at its opposite, upper end and of a smaller diameter. The insert 38 is a close fit within the aperture 37 through the flange 3, the aperture having a radially-enlarged recess 43 at its lower, patient end with a diameter and depth matched with the diameter and thickness of the lower head 41 of the insert so that this is a close fit in the recess. The flat, lower surface 44 of the insert 38 lies level with the lower, patient surface of the flange 3. The aperture 37 also has an enlarged recess 45 at its upper end of a smaller diameter than the lower recess 43. The head 42 at the upper, machine end of the insert has a diameter equal to that of the recess 45 at the upper end of the aperture 37. The upper surface 48 of the upper head 46 is domed to present a convex surface projecting slightly above the upper surface of the flange 3. In this way it can be seen that the heads 41 and 46 at opposite ends of the insert 38 overlap the flange 3 on both sides to ensure that the insert cannot fall out of or be separated from the flange, thereby removing any risk that the inserts drop off the tube during use.

Figure 5:
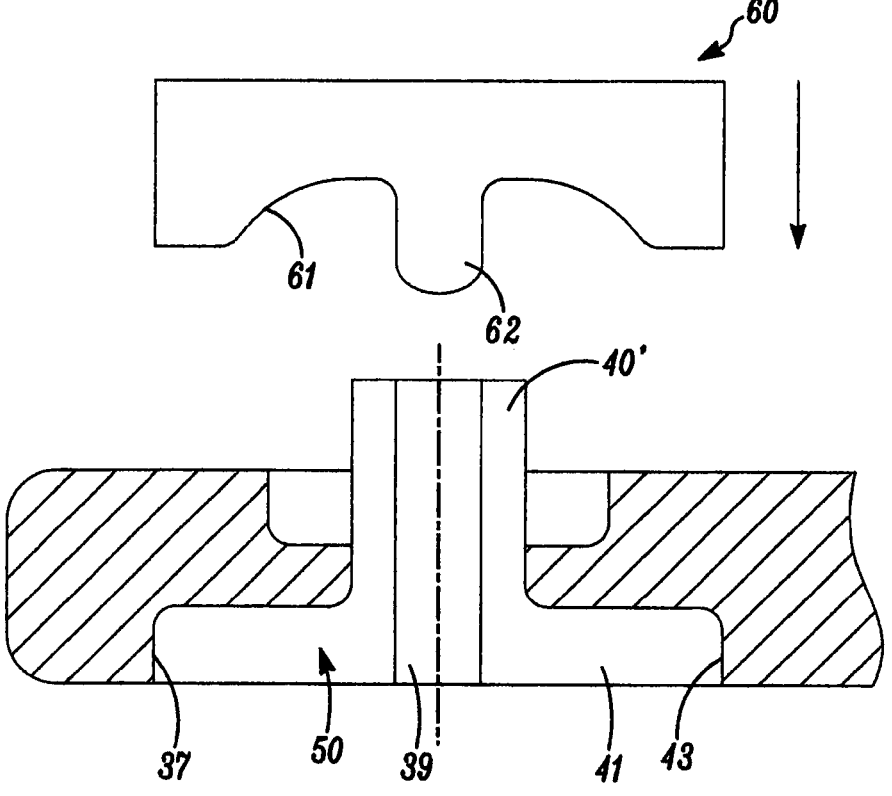
FIG. 5 illustrates a step in the assembly of the insert in the flange.

The inserts 38 are fixed with the apertures 37 in the flange 3 in the manner shown in FIG. 5. Each insert is initially provided as a preformed stud 50 with the lower head 41 but without the upper head and instead with an extended body portion 40'. This stud 50 is inserted in the aperture 37 from the lower surface of the flange 3 so that the lower head 41 locates in the lower recess 43 and the body portion 40' projects through the aperture and above the upper surface of the flange 3. A heated tool 60 is then brought down on the projecting end of the body portion 40' to soften this part of the insert 50 and deform it down into the upper recess 45. The lower surface of the heated tool 60 has a concave cavity

61, corresponding to the desired domed shape of the upper end 48 of the insert 38, and a central axial peg 62 with a diameter corresponding to that of the bore 39 through the insert so that this bore is not closed by flowed material. The tool 60 is then lifted and the insert 38 cools and hardens to the finished shape. The domed surface 48 of the insert 38 reduces the risk of sharp edges that could damage a suture, the neck tie, the patient or clinical staff.

Figure 6:
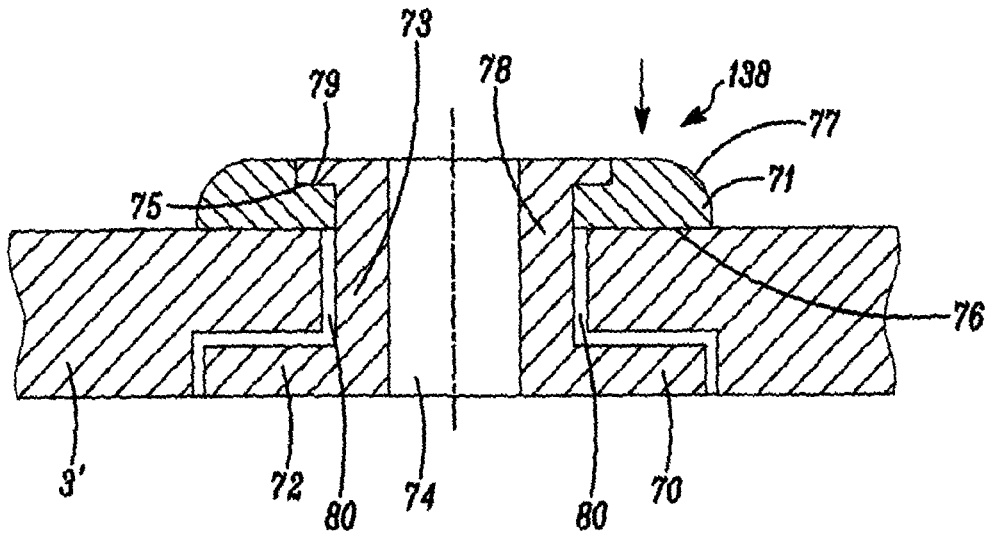
FIG. 6 is cross-sectional view of a part of an alternative reinforced flange.
Figure 7:
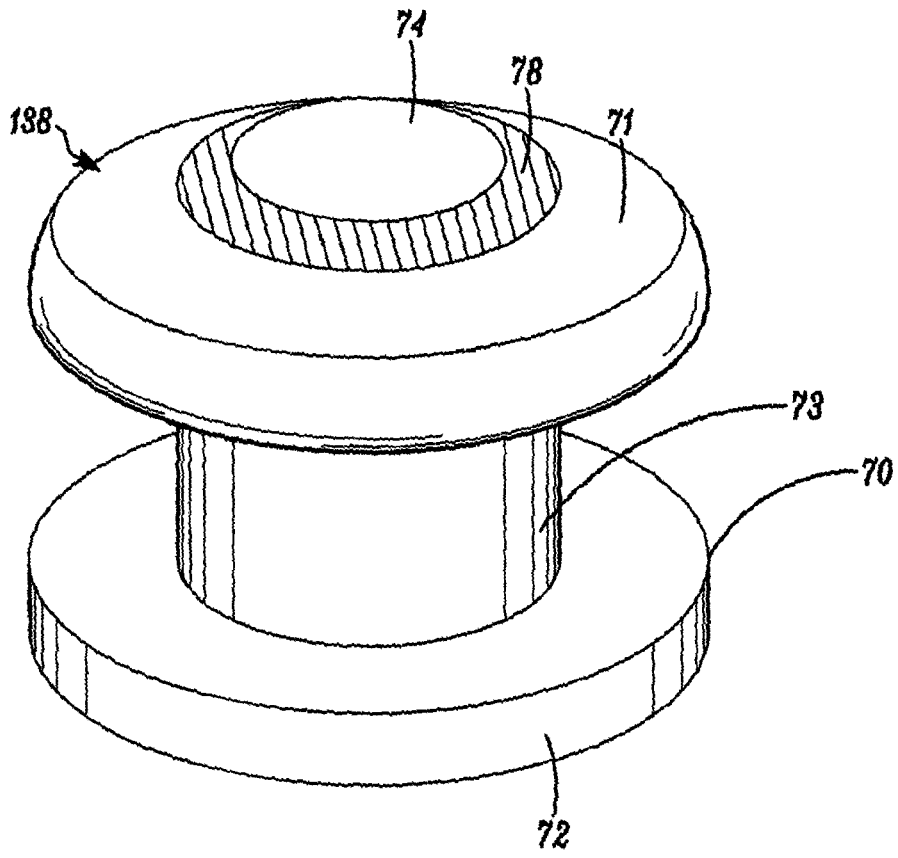
FIG. 7 is a perspective view of the insert used in the arrangement shown in FIG. 6.

Inserts could be retained in the flange openings in other ways than by heat forming a part of the insert over the surrounding part of the flange. FIGS. 6 and 7 show an alternative arrangement where an insert 138 is formed by two separate moulded components, namely a main component 70 and a retaining ring component 71 providing an upper, radially-extending head for the insert. The main component 70 comprises a lower enlarged head 72 and a hollow, tubular, axial body portion 73 with a passage or bore 74 extending through it. The outer edge of the body portion 73 at its upper end has a retaining clip formation 75 in the form of a downwardly facing lip. The outer diameter of the clip formation 75 is equal to or slightly smaller than the diameter of the smallest part of the opening 80 through the flange 3' so that the upper end of the main component 70 of the insert can be inserted through the aperture. The retaining ring component 71 has a flat lower surface 76, which lies against the upper surface of the flange 3', and has a rounded upper surface 77. The ring component 71 has a central opening 78 in which the upper end of the body portion 73 is retained, the ring having a retaining clip formation 79 around the inside of the opening formed by an upwardly facing lip. The retaining formations 75 and 79 on the main component 70 and the retaining ring component 71 are such that the ring component can be pushed down over the upper end of the main component and lock with the main component when the retaining clip formations engage one another.

Instead of using the mechanical locking arrangement shown in FIGS. 6 and 7 the main body portion and the retaining ring component could have smooth engaging surfaces and be secured with one another by bonding or ultrasonic welding.

Tracheostomy tubes according to the present invention can have various advantages. The moulding process used to form the tube can be simplified because the reinforcing inserts are not included at the moulding stage but are added at a subsequent stage. Existing mould tooling can be easily modified to form the apertures in the flange into which the retaining inserts are fixed. The inserts could be colour coded according to the size of the tube or some other feature. If the flange is moulded of a transparent or translucent material the colour of the inserts will be very conspicuous even when the flange lies against the neck. The reinforcing inserts enable the flange to be formed of a soft, conformable plastics without any risk that a neck tie or suture extending through the inserts will damage the flange and without any risk of the inserts separating from the tube.

Although the reinforcing inserts have been described as being of circular section they could, be of other shapes such as rectangular with the opening through the insert being in the form of a slot. This might be more suitable for strap-like neck ties.

The invention claimed is:

1. A tracheostomy tube comprising:
   a shaft with a patient end adapted to locate in a trachea and
   an elongate flange of a first plastics material with two opposite ends at a machine end of the shaft for securing the tube with a neck of a patient, the flange extending outwardly of the shaft and having respective openings towards each of the opposite ends, wherein each of the openings has a radially-enlarged recess around it on each of a patient-facing side of the flange adapted to face the patient and an opposite machine-facing side of the flange adapted to face away from the patient;

respective hollow inserts of a second plastics material harder than the first plastics material of the flange, the respective inserts each having a tubular body forming a passage extending axially along the tubular body between a patient end and a machine end;

wherein each insert is received in a corresponding one of the respective openings of the flange;

wherein each insert has a disc-shaped head on the patient end having a thickness equal to a depth of the corresponding radially-enlarged recess on the patient-facing side of the flange and adapted to closely fit with the corresponding radially-enlarged recess on the patient-facing side of the flange so as to form a smooth patient-facing surface of the flange, wherein the machine end of each insert is retained with the flange by an upper radially-enlarged domed head heat-formed to overlap the flange around the corresponding opening on the machine-facing side of the flange, wherein the domed head extends beyond the radially-enlarged recess on the machine-facing side of the flange so as to form a non-smooth machine-facing surface of the flange, and wherein the passage of each insert is configured to allow a neck tie or suture to extend therethrough to secure the tracheostomy tube with the neck of the patient.

2. The tracheostomy tube according to claim 1, wherein the hollow inserts are of circular cross section.

3. The tracheostomy tube according to claim 1, wherein the first plastics material of the flange is silicone.

4. A method of reinforcing neck tie or suture openings in a flange of a tracheostomy tube wherein the openings each have a radially-enlarged recess on each of a patient side of the flange and an opposite machine side of the flange, wherein for each of the openings the method comprises:

providing an insert having a patient end and a machine end and a tubular body forming a passage extending axially between the patient end and the machine end, one radially-enlarged head at the patient end of the insert, inserting the insert into the opening from the patient side of the flange so that the one radially-enlarged head of the insert closely fits in the radially-enlarged recess on the patient side of the flange and a patient end surface of the one radially-enlarged head lies flush with a patient end surface of the flange, and subsequently heat forming a radially-enlarged domed head at the machine end of the insert to overlie a first machine end surface of the flange around the opening and thereby retain the insert securely with the flange, wherein the domed head extends beyond the radially-enlarged recess on the machine side of the flange such that it does not lie flush with a second machine end surface of the flange, wherein the passage of the insert is configured to allow a neck tie or suture to extend therethrough to secure the tracheostomy tube with a neck of a patient.

5. A tracheostomy tube having a flange with neck tie or suture openings, wherein each of the openings is reinforced by a method comprising:

providing an insert for the opening having a patient end and a machine end and a tubular body forming a passage extending axially along the tubular body between the machine end and the patient end, one radially-enlarged head at the patient end of the insert, inserting the insert into the opening from a patient side of the flange so that the one radially-enlarged head of the insert closely fits in a radially-enlarged recess on a patient side of the flange and a patient end surface of the radially-enlarged head of the insert lies flush with a patient end surface of the flange, and subsequently heat forming a radially-enlarged domed head at the machine end of the insert to overlie a first machine end surface of the flange around the opening within a radially-enlarged recess on an opposite machine side of the flange and thereby retain the insert securely with the flange, wherein the domed head extends beyond the radially-enlarged recess on the machine side of the flange such that it does not lie flush with a second machine end surface of the flange, wherein the passage of the insert is configured to allow a neck tie or suture to extend therethrough to secure the tracheostomy tube with a neck of a patient.

* * * * *